United States Patent [19]

Gbogi et al.

[11] Patent Number: 5,275,806

[45] Date of Patent: Jan. 4, 1994

[54] TOPICAL COMPOSITIONS FOR PROTECTION AGAINST ULTRAVIOLET RADIATION

[75] Inventors: Emanuel O. Gbogi, Tarrytown; Fouad Z. Saleeb, Pleasantville, both of N.Y.

[73] Assignee: Kraft General Foods, Inc., Northfield, Ill.

[21] Appl. No.: 946,206

[22] Filed: Sep. 16, 1992

[51] Int. Cl.$^5$ .......................... A61K 7/40; A61K 7/42; A61K 9/06; A61K 9/10

[52] U.S. Cl. ........................................ 424/59; 424/60; 424/69; 514/938; 514/944; 514/969

[58] Field of Search ...................... 424/59, 60; 514/938

[56] References Cited

U.S. PATENT DOCUMENTS 2,377,188  5/1945  Schwenk et al. ...................... 424/59

OTHER PUBLICATIONS

Pharmaceutical Formulas, 1953 P.F. vol. I, pp. 110–128 12th edition, published at the Offices of the Chemist & Druggist.

*Primary Examiner*—Dale R. Ore
*Attorney, Agent, or Firm*—Linn I. Grim

[57] ABSTRACT

Disclosed are compositions useful for topical application to protect skin from ultraviolet radiation, which comprise effective amounts of the reaction product of a calcium compound such as calcium hydroxide, calcium oxide, or calcium carbonate, with citric acid, the reaction product exhibiting a calcium:citrate molar ratio of 2.50:2 to 2.95:2 and a 1% slurry of the reaction product in water at 25° C. exhibiting a pH value of about 4 to below 7.

20 Claims, No Drawings

TOPICAL COMPOSITIONS FOR PROTECTION AGAINST ULTRAVIOLET RADIATION

FIELD OF THE INVENTION

The present invention relates to protecting skin, especially human skin, from ultraviolet radiation and its deleterious effects. The present invention relates particularly to compositions for topical application to the skin to provide such protection.

Ultraviolet radiation is known to cause degradation of different materials, for instance, paint, plastics and human skin if they are not protected. Ultraviolet radiation between 290 nm and 320 nm ("UV-B") has been known to rapidly produce damage to the human skin. Also, the human skin has been known to be affected by UV radiation between 320-400 nm ("UV-A"). Erythema, edema and blister are some of the damages produced on skin on exposure. Studies have also shown that long time exposure to this radiation causes keratoses and carcinoma in human skin.

Most sunscreen agents have maximum absorption between 290-320nm regions. Some of them are toxic, non-stable, change color and have odors. This invention relates to a non-toxic, in fact, edible, odorless sunscreen agent that protects the human skin from all UV radiation (both A and B) and that is much more effective than titanium dioxide.

SUMMARY OF THE INVENTION

The present invention, in one aspect to be described further below, is a composition for protecting the skin from ultraviolet radiation upon topical application thereof to the skin, comprising in a cosmetically acceptable vehicle the reaction product of a calcium compound selected from the group consisting of calcium hydroxide, calcium oxide, calcium carbonate, and mixtures thereof with citric acid wherein said reaction product has a mole ratio of calcium to citrate of from 2.50:2 to 2.95:2 and a pH value in a 1% water slurry of said reaction product of about 4 to below 7 at 25° C., wherein said reaction product is present in said composition in an amount effective to protect the skin from ultraviolet radiation upon topical application of said composition to the skin.

Another aspect of the present invention is a method of protecting the skin from ultraviolet radiation, the method comprising the topical application to the skin of a reaction product described above, in an amount effective to protect the skin from such radiation.

DETAILED DESCRIPTION OF THE INVENTION

The present invention permits the user to protect the skin from ultraviolet radiation such as that which normally impinges on the skin upon exposure to a source such as the sun. By "protect" means reducing or eliminating the amount of ultraviolet radiation which contacts the skin from such source compared to the amount which would contact the skin in the absence of such protection.

The Reaction Product

The calcium citrate compounds used in this invention are reaction products of a calcium compound selected from the group consisting of calcium hydroxide, calcium oxide and calcium carbonate, with citric acid wherein said reaction product has a mole ratio of calcium to citric acid from 2.50:2 to 2.95 to 2, preferably 2.61 to 2.92 and pH value in a 1% water slurry of said reaction product about 4 to below 7 preferably about 4.0 to about 6.5 at 25° C.

In general, these calcium citrate crystals are prepared by spray drying a neutralization mixture prepared by neutralizing citric acid with a slurry of calcium carbonate or calcium oxide or hydroxide in water, e.g., a slurry of calcium hydroxide under controlled conditions to assure the production of the present new calcium citrate salts. Temperature, slurry solid content, rate of mixing of reactants and agitation time before spray drying are critical parameters in determining the physical characteristics of the final product.

In particular, the calcium citrate crystals are prepared by first neutralizing citric acid with calcium hydroxide while controlling the rate and conditions of the reaction as well as the degree of neutralization. In the present process, a calcium hydroxide aqueous slurry is reacted with a citric acid solution in water resulting in a strong exothermic reaction. The rate of reaction, concentration of reactants and varying conditions are all important factors in producing calcium citrate salts of the desired pH values, moisture content and particularly the desired particle size.

It is preferred to form two separate aqueous systems, one, a solution of citric acid and the second, a slurry of calcium hydroxide, oxide or carbonate and then mix the uniform slurry of calcium hydroxide or carbonate with the aqueous citric acid. The temperature of the mixture is not allowed to exceed about 60° C. The pH of the slurry so produced after thorough mixing should fall within the range of 4-6 and, if needed, should be adjusted to this range of pH. The slurry can be used as such or can be spray-dried or dried by other known drying steps.

The produced calcium citrate salt is very insoluble in water providing about 0.1% by weight solution at ambient temperature and slightly more soluble in hot water. During preparation of a batch and while waiting for spray drying of the batch, the salts are present in the insoluble form, a slurry of tiny crystals which form aggregates of varying particle size ranging from 5 to 100 microns. In present experience, the best products are obtained by using the following conditions.

The solids level of the aqueous slurry of calcium citrate salt is maintained at 20-26% and preferably at 22-24% by weight based on anhydrous salt. The slurry temperature during spray drying is from 80° F.-100° F. and preferably 80°-90° F. To avoid gel formation in the aqueous slurry, especially at temperatures below 70° F., and recrystallization which can occur on prolonged storage, spray drying of the aqueous slurry is effected within about 4-5 hours after slurry preparation. The slurry is spray dried at an inlet temperature of from about 425° F. to about 460° F. to deliver a free-flowing white powder with a moisture content of less than 6% and bulk density of from about 0.3 to about 0.7 g/cc. Extensive mixing and especially homogenization prior to spray drying should be avoided since the particles of salt may be broken down into finer crystals.

The calcium citrate crystals generally have the following characteristics:

| | |
|---|---|
| Bulk density | 0.33-0.66 g/cc |
| Granulation | 95% through U.S. 100 mesh or 150 microns |

| | |
|---|---|
| Rotatap, 8 min. | 10% maximum through U.S. 400 mesh or 38 microns |
| pH (1% by weight solution) | 4.0–6.5 |
| Appearance | free-flowing, white powder |

The salts are neutral or slightly acidic and have a well-defined crystal size. The salt can be employed in the form of the anhydrous salt or the hydrated salt. In the hydrated form, the salt can usually contain up to about 13–15% by weight of water of hydration. In general, it is preferred to use the salt in lower hydrated form with less than about 10% by weight of water of hydration. Of course, the hydrated salt can be dried to any level of water of hydration using known methods. On standing, the salt does not undergo any loss or gain of water during storage.

The calcium citrate employed in the present invention is in the form of small platelet crystals. The average length of the crystals is below 3.0 microns, preferably about 1.5 microns, width below 2.0 microns, preferably about 1 micron and thickness below 1 micron, preferably 0.1 to 0.2 micron. During preparation, clusters of these platelets aggregate together to form spherical particles that range from about 5 to about 100 microns in diameter. Such clusters are readily separable by mechanical stirring in water or by merely allowing the clusters to stand in water for protracted periods of time, e.g. overnight at room temperature. A most effective method for reducing the clusters to the individual platelets is the use of mechanical shear, as provided by a ball mill. Other mechanical stirring means that can be employed include homogenizers, microfluidizers or colloid mills.

When mixed with water, particularly at levels above about 10% by weight, the present spray-dried calcium citrate salt platelets cause a significant increase in the viscosity of the resulting composition. Thus, at 15% to 20% by weight the aqueous calcium citrate compositions are in the form of thick pastes resembling soft cheeses and margarines in consistency. At 20% and higher levels, the mixtures tend to solidify, especially when highly efficient mechanical shear is used.

Topical Vehicles

The compositions according to the present invention can comprise any cosmetically acceptable vehicle. By "cosmetically acceptable" is meant that the vehicle is inert to the skin and permits easy, even application to the skin of a thin film which contains the reaction product. Such vehicles can comprise any of a large variety of forms, including oil-in-water emulsions, water-in-oil emulsions, anhydrous compositions such as oil-based liquids, slurries, powders or pastes, and aqueous solutions, slurries and pastes.

Compositions according to this invention can include water as a vehicle, usually with at least one other cosmetically-acceptable vehicle.

Vehicles other than water that can be used in compositions according to the invention can include liquids or solids as emollients, solvents, humectants, thickeners and powders. Examples of each of these types of vehicles, which can be used singly or as mixtures of one or more vehicles, are as follows:

Emollients, such as stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, tallow, lard, olive oil, palm kernel oil, rapeseed oil, safflower seed oil, soybean oil, sunflower seed oil, olive oil, sesame seed oil, coconut oil, arachis oil, castor oil, acetylated lanolin alcohols, petrolatum, mineral oil, butyl myristate, isostearic acid, palmitic acid, isopropyl linoleate, lauryl lactate, myristyl lactate, decyl oleate, myristyl myristate;

Solvents such as ethyl alcohol, methylene chloride, isopropanol, acetone, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, gelatin;

Powders can include components such as chalk, talc, fullers earth, kaolin, starch, gums, colloidal silicon dioxide, sodium polyacrylate, tetra alkyl and/or trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate, zinc or magnesium stearate, zinc oxide and magnesium oxide. These components may also be used as thickeners in fluid or semifluid compositions.

Examples of additional composition types are found in *Encyclopedia of Chemical Technology*, Vol. 7, pages 146–150 and 155–160 (John Wiley & Sons, 1979), the disclosure of which is hereby incorporated herein by reference.

Examples of other conventional adjuncts, some of which can also function as vehicles, that may optionally be employed, include volatile and non-volatile silicones; silicone polymers; preservatives, such as a parahydroxy benzoate esters; humectants, such as butane-1,3-diol, glycerol, sorbitol, polyethylene glycol; stabilizers, such as sodium chloride or ammonium chloride; buffer system, such as lactic acid together with a base such as sodium hydroxide; oils and waxes, such as avocado oil, Evening Primrose oil, sunflower oil, beeswax, ozokerite wax, paraffin wax, lanolin, lanolin alcohol; emollients; thickeners; activity enhancers; colourants; whiteners; fragrances; and bactericides.

When it is desired that the composition is in the form of an emulsion, for instance as a cream or lotion, the composition should also contain an emulsifier component which is constituted of one or more emulsifiers chosen to provide the HLB (hydrophilic-lipophilic balance) appropriate to whether the aqueous or oil phase is the continuous phase, and appropriate to the choice of the particular component forming the solid phase. Suitable cosmetically acceptable emulsifiers abound and are well known to the cosmetic chemist. Examples include compounds having a long-chain alkyl or alkylene chain of 12 to 20 carbon atoms substituted with a polyoxyethylene ($-(CH_2O)_{4-20}-H$) group; and glycol or glycerol derivatives substituted with an alkyl or alkylene chain of 12 to 24 carbon atoms. Further examples are found in *Encyclopedia of Chemical Technology*, Vol. 8, pages 913–916 (John Wiley & Sons, 1979), which are hereby incorporated herein by reference.

Formulation and Use

The preferred technique for preparing the compositions of the present invention is simply to mix together the vehicle, including any optional ingredients, and the reaction product. Mixing can be carried out with any standard high-speed equipment for achieving intimate blending of the components.

While the composition can contain the reaction product in any desired concentration, satisfactory compositions can contain up to 5 wt. % or even up to 2 wt. % of the reaction product. Compositions containing up to 0.5 wt. % of the reaction product are effective as well.

The topical skin treatment composition of the invention can be formulated as a fluid, for example in a product such as a lotion, with or without an applicator such as a roll-ball applicator, or a container fitted with a pump to dispense the composition, for example as a cream or mousse, or simply in a non-deformable bottle or squeeze container. Alternatively, the composition of the invention may be semi-solid, for example as a cream, lotion, gel, paste or ointment, for use in conjunction with a suitable applicator, or simply in a tube or lidded jar.

In use, a small quantity of the composition, for example from 1 to 5 ml, is applied to the desired area of skin, from a suitable container or applicator and, if necessary, it is then spread over and/or rubbed into the skin, using the hand or fingers or a suitable device.

The present invention will be described further in the following examples:

EXAMPLE 1

A calcium citrate sample was prepared by reacting 2763.8 lbs. of citric acid with 1600 lbs. calcium hydroxide (97–98% $Ca(OH)_2$ by analysis) in 1433 gallons of water. The mole ratio of calcium hydroxide to citric acid was very slightly less than 3:2, actually 2.92:2. The citric acid (Pfizer fine granular, food grade) was mixed in a large batch tank with 675 gallons of cold water. The calcium hydroxide (Mississippi Lime, hydrated lime food code) was mixed in a separate batch tank with 675 gallons of cold water. The calcium hydroxide slurry is then pumped into the citric acid solution at a rate to deliver the entire slurry in 10–15 minutes. It is necessary to have good agitation during the entire reaction and mixing process. The remaining 83 gallons of water is used to rinse the calcium hydroxide tank and transport lines. Due to the heat of reaction, the temperature of the resultant slurry increased from an initial value of 15° C. (60° F.) to maximum of 57° C. (134° F.). After the reaction is complete, the batch is cooled to 80°–90° F. The final pH of this concentrated slurry (22% calcium citrate, dry basis) should fall within the range 3.8–4.6 or can be adjusted up or down using the reacting ingredients. The slurry is then dried via spray drying utilizing a rotary wheel (7600 rpm). The outlet temperature was adjusted to 225° F. and the inlet temperature was 450° F.

The calcium citrate powder obtained after spray drying was a free-flowing white powder with a moisture content less than 6.0% and a bulk density in the range 0.33–0.65 g/cc. The pH of a 1% slurry in water was 5.5. 95% of the powder passed through U.S. 200 mesh.

EXAMPLE 2

Spray-dried calcium citrate produced in accordance with Example 1 was mixed with water and then micromilled to obtain a fairly thick paste which does not require refrigeration using the following procedure.

Calcium citrate (2265 g.) was added to 9656 g. of water at room temperature. A fairly gritty slurry was obtained (19% calcium citrate, 81% water) that was maintained in suspension by using an electric stirrer. The suspension was then pumped and milled using a DynoMill filled with glass beads (Type KDL, manufactured by Willy A. Bachofen, AG Machinenfabrik, Basel, Switzerland). One pass through the Dyno-Mill was sufficient to produce a fairly smooth paste. This sample is stable for several months whether refrigerated or stored at room temperature. There was no crystal growth or loss of smoothness.

EXAMPLE 3

Experimental results are given below when anhydrous citric acid was neutralized using basic calcium salts (oxide and hydroxide). No calcium carbonate was used because of the large volumes of carbon dioxide released during the reaction. The table gives the number of mols of calcium oxide or hydroxide added to 2 mols of citric acid and the pH of a 1% aqueous slurry of the resultant spray dried calcium citrate salt. (After reaction, agitation and spray drying as described in Example 1, 1 g of the resultant calcium citrate salt was dispersed in 100 ml distilled water for pH measurements.)

TABLE 1

| MOLAR RATIO OF CITRIC:CALCIUM IN CALCIUM CITRATE | | |
|---|---|---|
| Citric Acid (Mol) | Calcium (Mol) | pH (1% Slurry in Water) |
| 2 | 2.375 | 3.95 |
| 2 | 2.613 | 4.04 |
| 2 | 2.850 | 4.64 |
| 2 | 2.910 | 5.25 |
| 2 | 2.910 | 5.33 |
| 2 | 2.92 | 5.5 |
| 2 | 2.99 | 7.28 |

Commercially available tricalcium citrate (3 moles of calcium to 2 moles of citric) shows a pH of 9–11 when tested as a 1% slurry in water at 25° C. It is evident from the table that the composition range of the calcium citrate used in the present invention is 2.5 to 2.95 moles of calcium per 2 moles of citrate for pH values in the range of 4–7.

The new calcium citrate salts used in this invention are distinct from tricalcium citrate which is commercial available (Pfizer, Inc.) as is obvious from the following data:

| Commercial Tricalcium Citrate (Pfizer. Inc.) | New Calcium Citrate Salts of The Invention | |
|---|---|---|
| 10.66 | Moisture | less than 5.5 |
| 17.64 | % Ca | 22.16 |
| 19.74 | % Ca (dry wt.) | 23.7 |
| 9–11 | pH | 4–7 |

EXAMPLE 4

0.3 grams of a calcium citrate reaction product prepared in accordance with Example 1 having a calcium to citric acid mole ratio of 2.92 to 2, was dispersed in 99.7 grams of mineral oil. Separately, 0.3 grams of titanium dioxide was dispersed into 99.7 grams of mineral oil. The ultraviolet transmittance of each sample was tested, at identical conditions, from 200 nm to 400 nm. The results indicated that the transmittance of the composition containing titanium dioxide was twice that of the composition containing the calcium citrate reaction product, throughout the spectrum tested.

The present invention thus provides numerous significant advantages. It provides protection against the full range of wavelengths characteristic of ultraviolet radiation. It does so with even only a minor amount of active ingredient. That active ingredient, in turn, is readily formulatable into a wide variety of topical compositions, easy to prepare, non-harmful to the skin even in large amounts, non-offensive and is indeed so safe it is edible and recognized by the U.S. Food and Drug Administration as GRAS (Generally Recognized As Safe). The inventive compositions are stable, both as to physical form and as to ultraviolet absorbing capability.

What is claimed is:

1. A composition for protecting the skin from ultraviolet radiation upon topical application thereof to the skin, comprising in a cosmetically acceptable vehicle the reaction product of a calcium compound selected from the group consisting of calcium hydroxide, calcium oxide, calcium carbonate, and mixtures thereof with citric acid wherein said reaction product has a mole ratio of calcium to citrate of from 2.50:2 to 2.95:2 and a pH value in a 1% water slurry of said reaction product of about 4 to below 7 at 25° C., wherein said reaction product is present in said composition in an amount effective to protect the skin from ultraviolet radiation upon topical application of said composition to the skin.

2. A composition in accordance with claim 1 wherein said reaction product has a mole ratio of calcium to citrate of from 2.61:2 to 2.92:2.

3. A composition in accordance with claim 1 wherein said reaction product has a pH value in a 1% water slurry of said reaction product of from about 4.0 to about 6.5.

4. A composition in accordance with claim 2 wherein said reaction product has a pH value in a 1% water slurry of said reaction product of from about 4.0 to about 6.5.

5. A composition in accordance with claim 1 wherein said reaction product comprises up to about 5 wt. % of said composition.

6. A composition in accordance with claim 1 wherein said reaction product comprises up to about 1 wt. % of said composition.

7. A composition in accordance with claim 1 wherein said vehicle is an oil-in-water emulsion.

8. A composition in accordance with claim 1 wherein said vehicle is a water-in-oil emulsion.

9. A composition in accordance with claim 1 wherein said vehicle is anhydrous.

10. A composition in accordance with claim 1 wherein said vehicle is an aqueous solution, slurry, or paste.

11. A method for protecting the skin from ultraviolet radiation comprising topically applying to the skin an amount effective to protect the skin from said radiation of the reaction product of a calcium compound selected from the group consisting of calcium hydroxide, calcium oxide and calcium carbonate and mixtures thereof with citric acid wherein said reaction product has a mole ratio of calcium to citrate from 2.50:2 to 2.95:2 and a pH value in a 1% water slurry of said reaction product of about 4 to below 7 at 250° C.

12. A method in accordance with claim 11 wherein said reaction product has a mole ratio of calcium to citrate of from 2.61:2 to 2.92:2.

13. A method in accordance with claim 11 wherein said reaction product has a pH value in a 1% water slurry of said reaction product of from about 4.0 to about 6.5.

14. A method in accordance with claim 13 wherein said reaction product has a mole ratio of calcium to citrate of from 2.61:2 to 2.92:2.

15. A method in accordance with claim 11 which comprises topically applying to the skin a composition comprising up to about 5 wt. % of said reaction product.

16. A method in accordance with claim 11 which comprises topically applying to the skin a composition comprising up to about 1 wt. % of said reaction product.

17. A method in accordance with claim 11 which comprises topically applying to the skin an oil-in-water emulsion containing said reaction product.

18. A method in accordance with claim 11 which comprises topically applying to the skin a water-in-oil emulsion containing said reaction product.

19. A method in accordance with claim 11 which comprises topically applying to the skin an anhydrous composition containing said reaction product.

20. A method in accordance with claim 11 which comprises topically applying to the skin an aqueous solution, slurry, or paste containing said reaction product.

* * * * *